(12) United States Patent
Wasielewski (10) Patent No.: US 7,615,083 B2
(45) Date of Patent: Nov. 10, 2009

(54) BIOLOGICALLY REABSORBABLE ACETABULAR CONSTRAINING COMPONENTS AND MATERIALS FOR USE WITH A HIP REPLACEMENT PROSTHESIS AND BIOREABSORBABLE MATERIALS TO AUGMENT HIP REPLACEMENT STABILITY AND FUNCTION

(75) Inventor: Ray C. Wasielewski, New Albany, OH (US)

(73) Assignee: Orthowaz, Ltd., New Albany, OH (US)

( * ) Notice: Subject to any disclaimer, the term of this patent is extended or adjusted under 35 U.S.C. 154(b) by 425 days.

(21) Appl. No.: 11/120,884

(22) Filed: May 3, 2005

(65) Prior Publication Data

US 2005/0216091 A1 Sep. 29, 2005

Related U.S. Application Data

(62) Division of application No. 10/392,553, filed on Mar. 20, 2003, now Pat. No. 6,923,833.

(60) Provisional application No. 60/371,058, filed on Apr. 9, 2002.

(51) Int. Cl.
*A61F 2/32* (2006.01)
(52) U.S. Cl. ................. 623/22.15; 623/22.11; 623/22.2
(58) Field of Classification Search .............. 623/22.11, 623/22.19, 22.15, 22.2, 22.28, 22.29, 22.36, 623/22.37, 23.11, 23.27, 23.26, 23.29, 23.36, 623/23.39
See application file for complete search history.

(56) References Cited

U.S. PATENT DOCUMENTS 3,722,002 A 3/1973 Charnley
4,963,489 A * 10/1990 Naughton et al. ............ 435/1.1
5,133,763 A * 7/1992 Mullers .................... 623/22.15
5,378,228 A 1/1995 Schmalzried et al.

(Continued)

FOREIGN PATENT DOCUMENTS

DE 3200340 A1 9/1982

(Continued)

OTHER PUBLICATIONS

Hopson, Krista, A Hip Alternative: Ceramic-on Ceramic Hip Implant Let Patients Stay Active Longer, UMHS Press Release: Hip Replacement, Apr. 8, 2003, 3 pages, University of Michigan Health System, Ann Arbor, MI, copyright 2003.

(Continued)

*Primary Examiner*—Pedro Philogene
(74) *Attorney, Agent, or Firm*—Taft Stettinius & Hollister LLP (57) ABSTRACT

A prosthetic constraining device for use with a hip replacement prosthesis that includes an acetabular cup assembly adapted to be bonded to a patient's pelvis and a femoral stem adapted to be bonded to the patient's femur, where the femoral stem includes a ball component at its proximal end received within the acetabular cup assembly to form a ball joint type coupling, and where the constraining device includes a ring having a central aperture, where the ring is adapted to be mounted to a rim of the acetabular cup assembly so that the femoral stem passes through the central aperture, where the diameter of the central aperture is less than the diameter of the ball component on the proximal end of the femoral stem so that the ring assists in maintaining the ball joint type coupling between the acetabular cup assembly and the femoral stem, and where the ring comprises a biologic material, a biologically reabsorbable material and a combination of biologic, or biologically reabsorbable materials.

7 Claims, 8 Drawing Sheets

U.S. PATENT DOCUMENTS

| | | | |
|---|---|---|---|
| 5,571,193 A | 11/1996 | Kampner | |
| 5,735,901 A | 4/1998 | Maumy et al. | |
| 5,763,399 A | 6/1998 | Lee | |
| 5,997,582 A | 12/1999 | Weiss | |
| 6,096,083 A * | 8/2000 | Keller et al. | 623/22.11 |
| 6,132,470 A * | 10/2000 | Berman | 623/23.15 |
| 6,214,014 B1 | 4/2001 | McGann | |
| 6,228,122 B1 * | 5/2001 | McGann | 623/23.11 |
| 6,241,771 B1 | 6/2001 | Gresser et al. | |
| 6,695,884 B1 * | 2/2004 | Townley | 623/23.26 |
| 6,923,833 B2 * | 8/2005 | Wasielewski | 623/22.11 |
| 2001/0008980 A1 | 7/2001 | Gresser et al. | |
| 2002/0022861 A1 * | 2/2002 | Jacobs et al. | 606/216 |

FOREIGN PATENT DOCUMENTS

| | | |
|---|---|---|
| DE | 4239263 A1 | 5/1994 |
| DE | 19716051 A1 | 11/1997 |
| WO | WO 97/14447 | 4/1997 |
| WO | WO 00/13615 | 3/2000 |
| WO | WO 00/15765 A1 | 3/2000 |
| WO | WO 02/09615 A2 | 2/2002 |
| WO | PCT/US03/10950 | 7/2004 |

OTHER PUBLICATIONS

McConway, et al., The use of a posterior lip augmentation device for a revision of recurrent dislocation after primary cemented Charnley/Charnley Elite total hip replacement, J Bone Joint Surg (Br) 2007;89-B:1581-5, © 2007 British Editorial Society of Bone and Joint Surgery, UK.

* cited by examiner

BIOLOGICALLY REABSORBABLE ACETABULAR CONSTRAINING COMPONENTS AND MATERIALS FOR USE WITH A HIP REPLACEMENT PROSTHESIS AND BIOREABSORBABLE MATERIALS TO AUGMENT HIP REPLACEMENT STABILITY AND FUNCTION

REFERENCE TO RELATED APPLICATION

This application is a divisional of U.S. patent application Ser. No. 10/392,553 entitled, "BIOLOGICALLY REABSORBABLE ACETABULAR CONSTRAINING COMPONENTS AND MATERIALS FOR USE WITH A HIP REPLACEMENT PROSTHESIS AND BIOREABSORBABLE MATERIALS TO AUGMENT HIP REPLACEMENT STABILITY AND FUNCTION ", filed on Mar. 20, 2003 now U.S. Pat. No. 6,923,833, which claimed the benefit of U.S. Provisional Application Ser. No. 60/371,058, entitled "BIOLOGICALLY ABSORBABLE ACETABULAR CONSTRAINING COMPONENTS AND MATERIALS FOR USE WITH A HIP REPLACEMENT PROSTHESIS AND BIOABSORBABLE MATERIALS TO AUGMENT HIP REPLACEMENT STABILITY AND FUNCTION", filed on Apr. 9, 2002, the disclosure of which is incorporated herein by reference.

BACKGROUND

1. Field of the Invention

The present invention is directed toward constraining components for use with joints of the body. Examples of such joints include hip joints, shoulder joints, elbow joints, and ankle joints. More specifically, aspects of the present invention are directed toward biologic and biologically reabsorbable acetabular constraining components to at least temporarily augment the stability and function of the joint after repair or replacement surgery.

2. Background of the Invention

Figure 1:
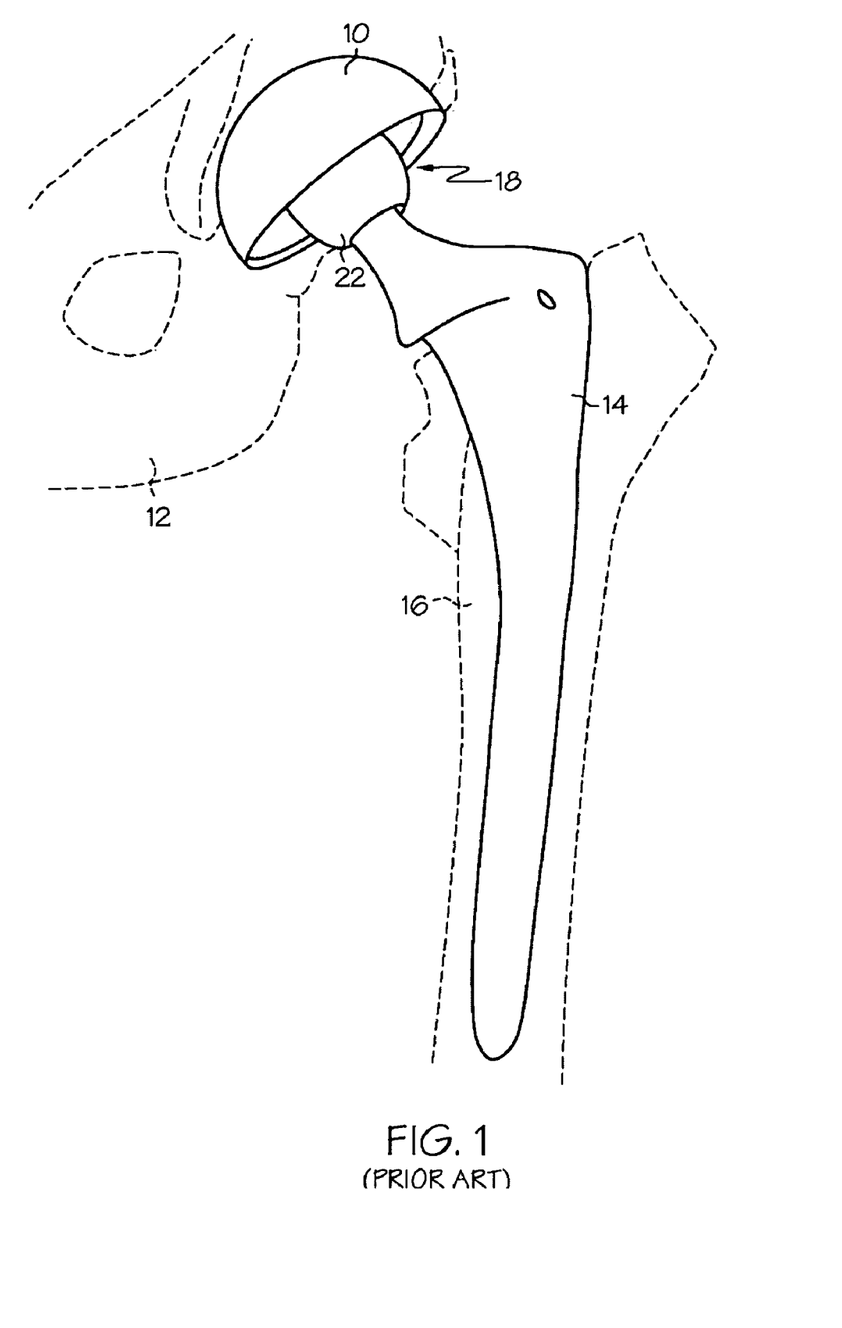
FIG. 1 is a perspective view of a prior art femoral prosthesis fitted within a prior art acetabulum prosthesis.
Figure 2:
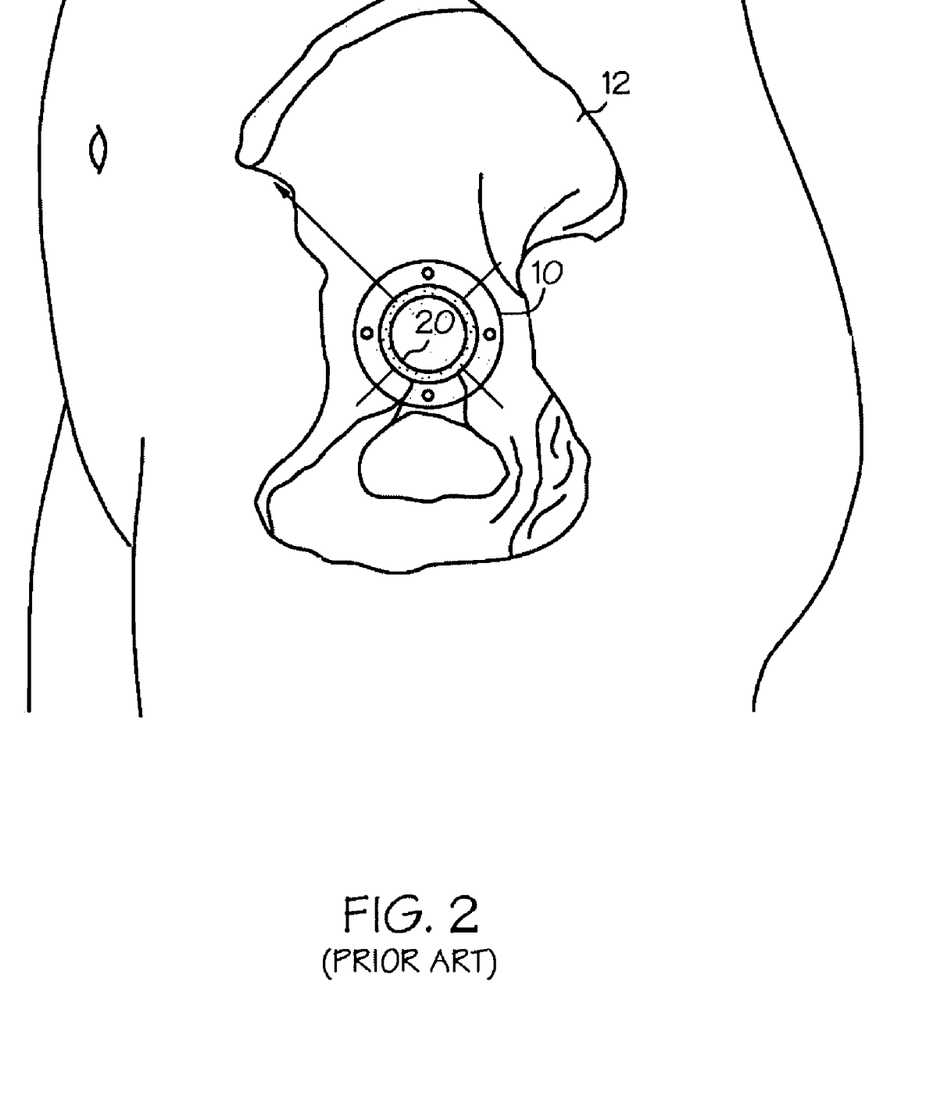
FIG. 2 is a side representative view of a prior art acetabulum prosthesis implanted within the pelvis.

FIG. 1 illustrates a prior art hip replacement prosthesis which includes an acetabular cup/shell 10 bonded to the pelvis 12 of a patient and a femoral component 14 or stem bonded to the patient's femur 16 where the acetabular cup/shell 10 and femoral component 14 are coupled together with a ball joint-type coupling 18. FIG. 2 illustrates a side view of the acetabular shell 10 bonded to the patient's pelvis 12. The acetabular shell includes a polyethylene, metal, or ceramic insert 20 seated therein.

A frequent complication with prior art hip replacement prosthetic components is dislocation of the ball 22 of the femoral component 14 from the acetabular shell 10. Prior art attempts to overcome this problem utilize constraining mechanisms, such as locking rings. However, such constraining mechanisms may tend to limit hip range of motion permanently, may not allow for normal pari-articular scarring to occur to optimize long-term hip stability and range of motion, and may also increase stress transmission to the fixation interfaces of the acetabular shell 10 over time promoting mechanical breakdown of ingrowth or cement and/or locking mechanism failure between the acetabular shell 10 and polyethylene insert 20 resulting in backside acetabular wear.

SUMMARY

The present invention is directed to constraining devices that assist in inhibiting dislocation of a ball aspect of a prosthetic hip joint after surgery. Certain aspects of the present invention are directed to the use of a constraining mechanism for a prosthetic hip implant that is made of biologic and/or biologically reabsorbable material affixed between the acetabular cup and the femoral component of a hip prosthesis. Further aspects of the present invention are directed toward the use of biologic and/or biologically reabsorbable material to increase the rate of tissue formation (such as scar tissue formation) and subsequent time to host stability about the total hip replacement. Further aspects of the present invention are directed to the use of a biologic and/or biologically reabsorbable paste or glue material (either alone or in combination with any of the above aspects) to increase the rate of scar tissue formation and subsequent host stability about the hip joint after total hip replacement. Further aspects of the present invention are directed to the impregnation of helpful agents to any of the above biologic and biologically reabsorbable materials such as a clotting agent, a scarring agent, a preventative bone formation agent (anti-heterotopic ossification), a non-steroidal anti-inflammatory drug (NSAID), and/or an antibiotic. Further aspects of the present invention are directed to the use of a biologic and/or biologically reabsorbable stabilizer that could span from the acetabulum and be fixed to the neck of the femoral component to act like a rubber band allowing motion of the femoral component while eventually scaring to provide permanent stability, used alone or in combination with any of the other aspects described above. Further aspects of the present invention are directed to the use of biologically reabsorbable screws or other fasteners to attach a constraining mechanism to the acetabular cup/shell (used either alone or in combination with any of the above aspects). Further aspects of the present invention are directed to the use of biologically reabsorbable mesh or webbing to retain the femoral component to the acetabulum or acetabular cup/shell component, used either alone or in combination with any of the above aspects.

Particular embodiments make use of constraining rings having geometries that are specifically adapted to provide the range of motion desired by patients after surgery, but with the additional benefit of doing so without substantially increasing the risks of impingement on the femoral component neck at the extremes of motion or dislocation and additional surgery to repair the dislocation. At least one of the exemplary embodiments utilizes a biologically reabsorbable material to temporarily inhibit such dislocation, allowing the physician to position and/or rotate the constraining device to reduce impingement and increase the available range of motion desirable in at least one axial direction. In such an embodiment, it is envisioned that the biologically reabsorbable material degrades in general proportion to the level of tissue developed by the patient's own body to supplement stability of the hip joint and inhibit dislocation. Thus, as the patient's need for an artificial constraining device decreases, so too does the artificial constraining device itself.

It is an aspect of the present invention to provide a prosthetic constraining device for use with a hip replacement prosthesis that includes an acetabular cup assembly adapted to be bonded to a patient's pelvis and a femoral stem adapted to be bonded to the patient's femur, where the femoral stem includes a ball component at its proximal end received within the acetabular cup assembly to form a ball joint type coupling, and where the constraining device includes a ring having a central aperture, where the ring is adapted to be mounted to a rim of the acetabular cup assembly so that the femoral stem passes through the central aperture, where the diameter of the central aperture is less than the diameter of the ball component on the proximal end of the femoral stem so that the ring assists in maintaining the ball joint type coupling between the acetabular cup assembly and the femoral stem, and where the ring comprises a biologic material, a biologically reabsorbable material or a combination of biologic, and biologically reabsorbable materials.

It is a second aspect of the present invention to provide a prosthetic hip prosthesis that includes: an acetabular cup assembly adapted to be bonded to a patient's pelvis; a femoral stem adapted to be bonded to the patient's femur, where the femoral stem includes a ball component at its proximal end received within the acetabular cup assembly to form a ball joint type coupling; and, a constraining ring having a central aperture, mounted to a rim of the acetabular cup assembly so that the femoral stem passes through the central aperture, where the diameter of the central aperture is less than the diameter of the ball component on the proximal end of the femoral stem so that the ring assists in maintaining the ball joint type coupling between the acetabular cup assembly and the femoral stem, and where the constraining ring comprises a biologic material, a biologically reabsorbable material, or a combination of biologic and biologically reabsorbable materials.

It is a third aspect of the present invention to provide a prosthetic constraining device for implantation in proximity to a hip joint that includes an arcuate body defining a central aperture for allowing a femoral component to extend therethrough, where the arcuate body includes a distal surface having at least one depression extending radially thereacross to provide an increased range of angular motion of the femoral component, and including a proximal surface adapted to be mounted to an acetabular prosthesis, an acetabular bone, and/or an innominate bone to help prevent a femoral head of the femoral component from completely passing distally through the aperture.

It is a fourth aspect of the present invention to provide a constraining device for, at least temporarily, maintaining engagement of a prosthetic femoral stem component with a prosthetic acetabular component of a prosthetic hip assembly, where the constraining device comprises a biologic material, a biologically reabsorbable material, or a combination of biologic and biologically reabsorbable materials.

It is a fifth aspect of the present invention to provide an implantable constraining device for, at least temporarily, maintaining the integrity of a hip joint, where the constraining device comprises a biologic material, a biologically reabsorbable material, or a combination of biologic and biologically reabsorbable materials.

It is a sixth aspect of the present invention to provide a constraining device for implantation in proximity to a hip joint that includes a plate comprising at least one biologically reabsorbable material, having an aperture extending therethrough for allowing a femoral component to extend therethrough, where the plate includes a distal surface having at least one depression accommodating an increased range of angular motion of the femoral component, and includes a proximal surface adapted to be mounted to an acetabular prosthesis, an acetabular bone, and/or an innominate bone to assist in inhibiting a femoral head of the femoral component from completely passing distally through the aperture.

A seventh aspect of the present invention is directed to a method for providing at least temporary stability to a prosthetic hip joint which includes an acetabular cup assembly bonded to a patient's pelvis and a femoral stem bonded to the patient's femur, where the femoral stem includes a ball component at its proximal end received within the acetabular cup assembly to form a ball joint type coupling. The method includes the step of mounting a constraining device to the prosthetic hip joint to provide stability to the prosthetic hip joint, where the constraining device comprises a biologic material, a biologically reabsorbable material, or a combination of biologic and biologically reabsorbable materials.

DESCRIPTION OF THE PRESENT INVENTION

The exemplary embodiments described herein relate to constraining devices, materials and techniques for use in hip replacement surgery. It will, of course, be apparent to those of ordinary skill in the art that the devices, materials and techniques disclosed herein may be useful for other types of implants and orthopedic surgeries.

Figure 3:
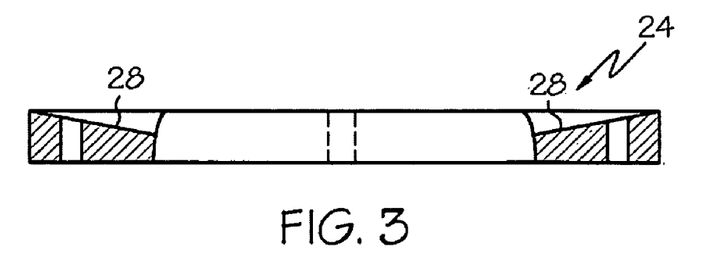
FIG. 3 is a cross-sectional, side elevational view taken along lines 3-3 of FIG. 4.
Figure 4:
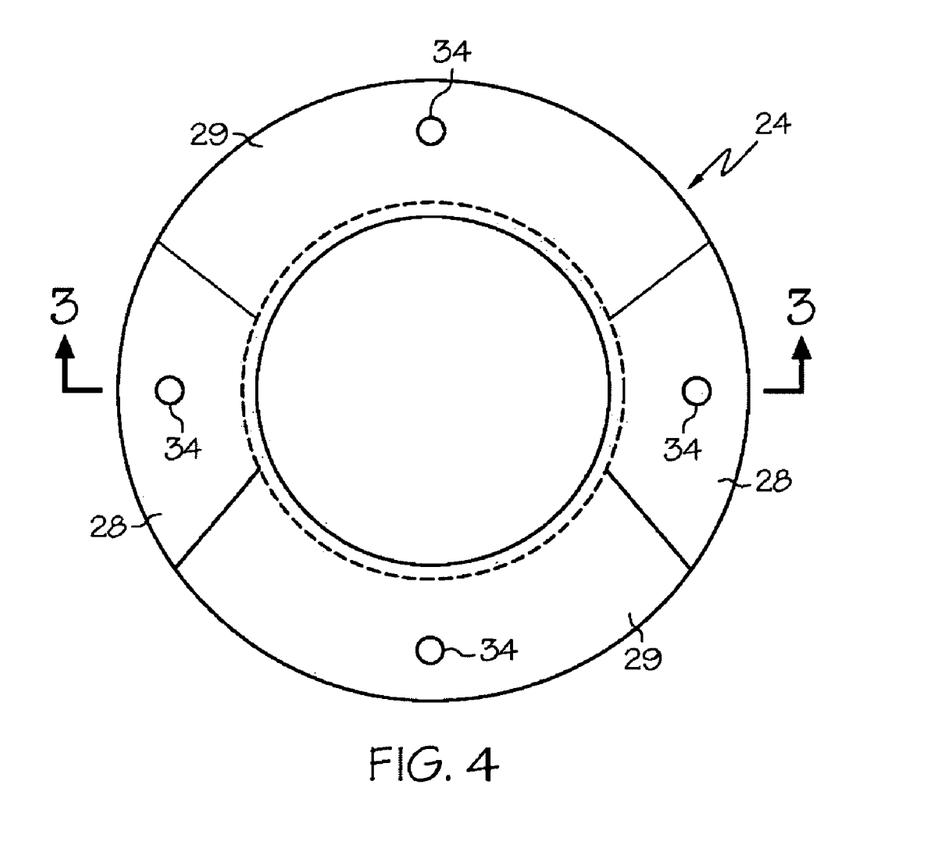
FIG. 4 is a top plan view of a first exemplary embodiment of the present invention.
Figure 5:
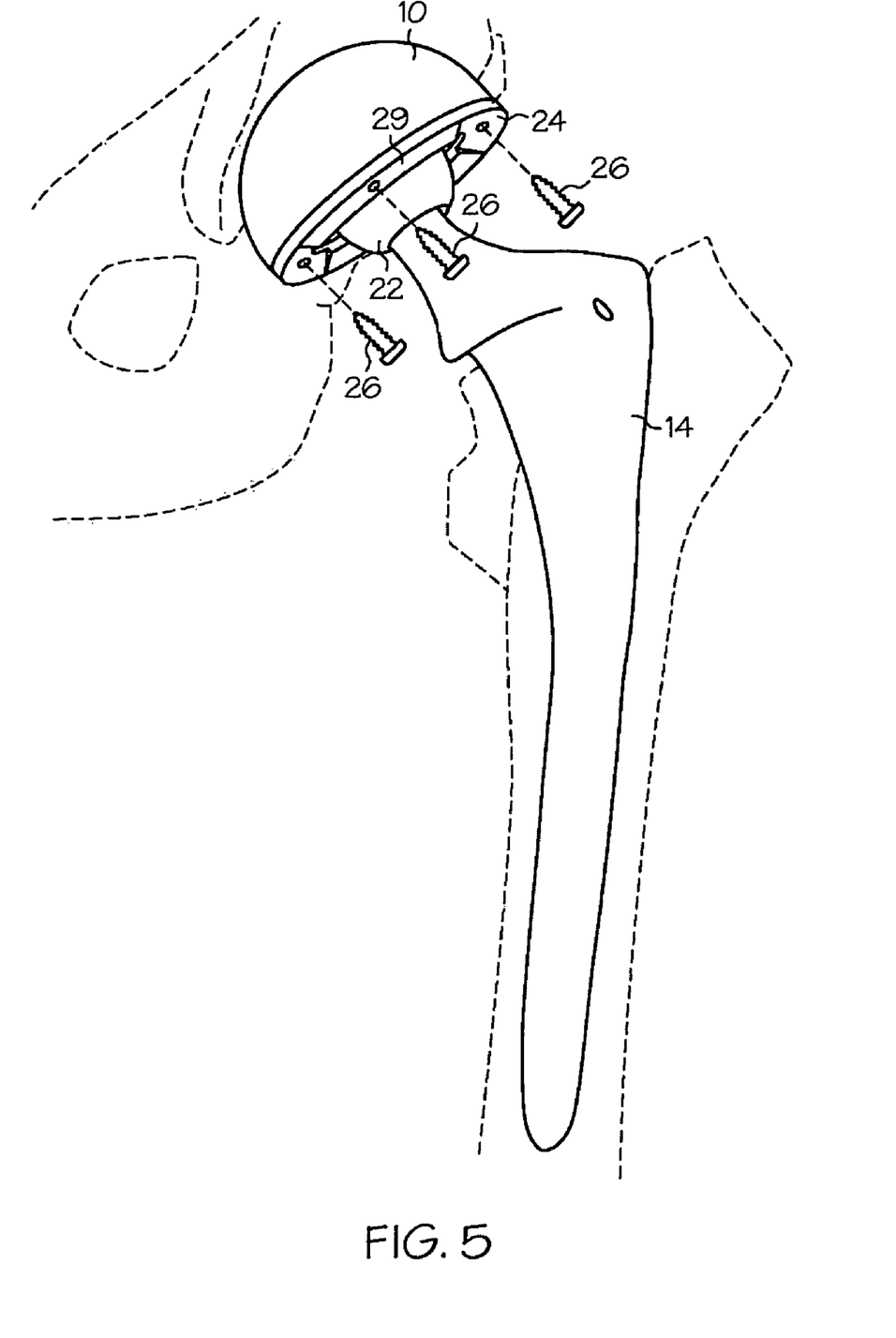
FIG. 5 is a perspective view of the first exemplary embodiment of the present invention being mounted to the acetabular prosthetic cup.

As shown in FIGS. 3-5, a first exemplary embodiment of the present invention is a constraining ring 24 adapted to be mounted on a distal end of the acetabular shell 10 (see FIG. 5) for maintaining the ball 22 of the femoral component 14 within the acetabular shell 10. The constraining ring 24 is comprises a biologic and/or a biologically reabsorbable material that provides temporary stability to the hip joint for varying times until live tissue (such as scar tissue) forms and replaces the biologic and/or biologically reabsorbable material or stability is achieved through normal host compensatory mechanisms.

In an exemplary procedure, a physician would position the constraining ring 24 around the neck of the femoral component 14 and thereafter attach the ball 22 to the end of the neck of the femoral component 14. This effectively maintains the position of the constraining ring 24 between the ball 22 and the base of the neck, as the cross section of the opening of the constraining ring 24 does not accommodate throughput of the ball 22 or the base of the neck of the femoral component 14. After the physician has seated the ball 22 in the acetabular insert 20, the constraining ring 24 is mounted onto the distal rim of the acetabular shell 10 with reabsorbable fasteners, such as, without limitation, clips, snaps, screws, sutures, and rivets 26. It is likewise possible that the constraining ring 24 be mounted to the acetabular bone or the innominate bone, or to the acetabular insert 20. The constraining ring 24 acts to inhibit post-operative dislocation of the ball 22 from the acetabular shell 10.

The reabsorbable constraining ring 24 of this exemplary embodiment includes angled cut out regions 28 (or cut-away regions) formed into the distal end of the constraining ring 24 and positioned radially on the anterior/superior and posterior/superior portions of the constraining ring 24 to improve range of motion for the femoral component 14, while inhibiting dislocation. Typically, these cut out regions 28 would be positioned anteriorly to mitigate posterior dislocation when the hip is flexed and internally rotated. Conversely, these cut out regions 28 may be located posteriorly to mitigate anterior dislocation by inhibiting posterior impingement when the hip is externally rotated and extended. Further, the constraining ring 24 may also have an elevation(s) 29 that may be positioned to further augment stability. The interior surface of the constraining ring 24 may be contoured to better approximate the contour of the ball 22, exhibiting generally greater cross section from proximal to distal end. In other words, the constraining ring 24 includes an inner surface that is substantially dome-shaped terminating at the aperture and having a diameter that narrows with the distance away from the proximal surface of the constraining ring 24.

In this exemplary embodiment, the constraining ring 24 will be absorbed over a relatively short period (i.e., several weeks or months) and be replaced by tissue (such as scar tissue) that provides for long-term hip stability and, hopefully, normal range of motion.

Examples of biologic materials for use with the constraining ring 24 include, without limitation, extra cellular matrices (ECMs). Examples of ECMs include, without limitation, porcine small intestine submucosa (SIS), xenogeneic small intestine submucosa (xSIS), urinary bladder submucosa (UBS), laminated intestinal submucosa, glutaraldehyde-treated bovine pericardium (GLBP). The biologic materials may be layered, molded, formed, braided, perforated, multilaminated, grafted or otherwise manipulated to achieve the desired properties and dimensions associated with the constraining ring 24.

Examples of biologically reabsorbable materials for use with the constraining ring 24 include, without limitation, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The biologically reabsorbable materials may be layered, molded, formed, braided, perforated, multilaminated, grafted or otherwise manipulated to achieve the desired properties and dimensions associated with the constraining ring 24. For example, the MONOCRYL (poliglecaprone 25), PDS II (polydioxanone), and resorbable plate materials may be block formed, while the surgical gut suture (SGS), gut, coated VICRYL (polyglactin 910), human autograft tendon material, collagen fiber, POLYSORB, poly-L-lactic acid (PLLA), polylactic acid (PLA), polyglycolic acid, and porcine small intestinal submucosa (SIS) material may be layered and formed. It is within the scope and spirit of the present invention that any of the above materials and techniques may be used individually, alternatively, or in conjunction to produce the constraining ring 24.

Exemplary materials comprising the biologically reabsorbable screws 26 include, without limitation, poly-L-lactic acid (PLLA) and collagen. As will be apparent to those of ordinary skill in the art, there are many other biologic and/or biologically reabsorbable materials that can be used for the constraining ring 24 or screws 26, all of which and others developed hereafter fall within the scope of the invention.

It is also within the scope of the present invention to "load" (disburse, coat, impregnate, etc.) the biologic and/or biologically reabsorbable material comprising the constraining ring 24 with agents that could hasten or assist in tissue development, prevent unwanted bone formation (including heterotopic ossification), and/or fight infection. Exemplary agents include, for example, without limitation, concentrated platelets (SYMPHONY from Depuy Orthapedic) and gentamicin.

Figure 6:
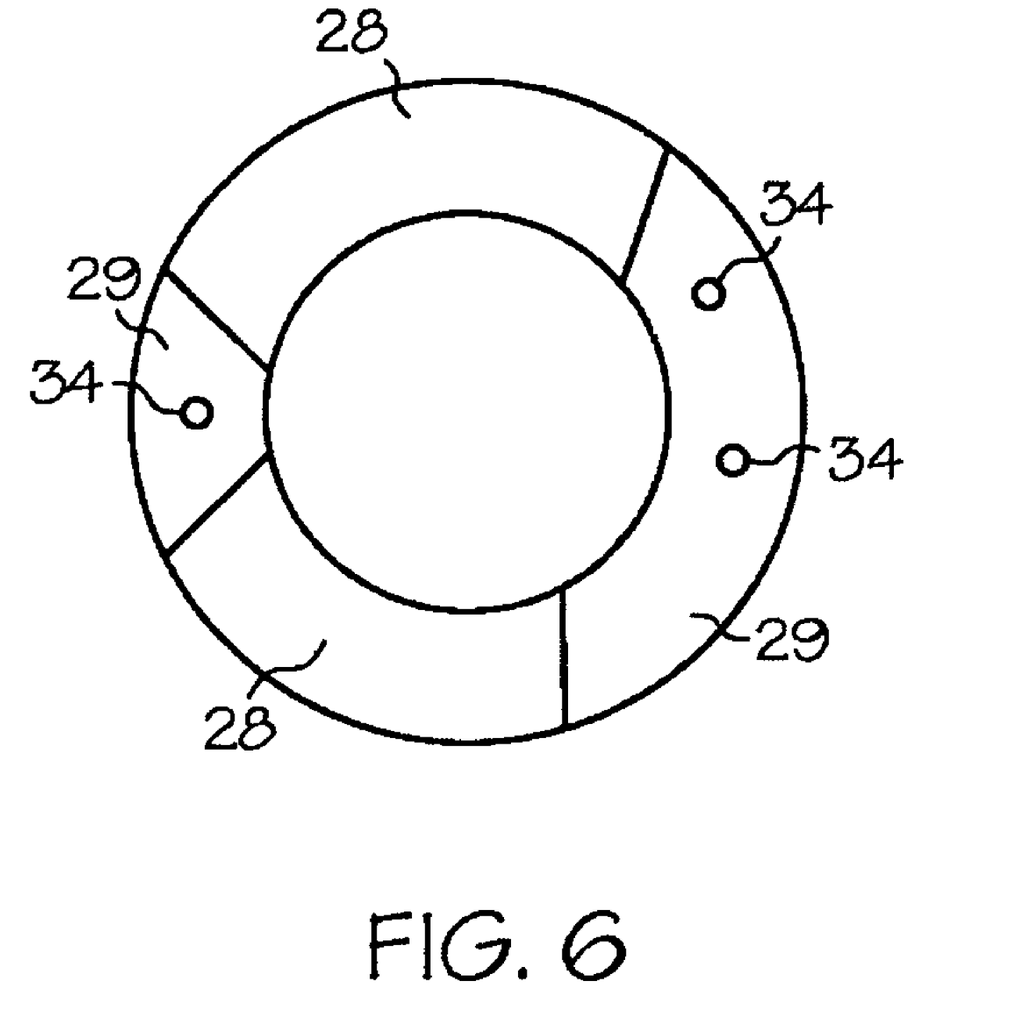
FIG. 6 is a top plan view of one of many possible alternate configurations for the first exemplary embodiment of the present invention.

FIG. 6 illustrates an alternate exemplary embodiment of the constraining ring 24, having an alternate screw-hole 34 pattern, angled cut out region 28 pattern, and elevation 29 pattern.

Figure 7:
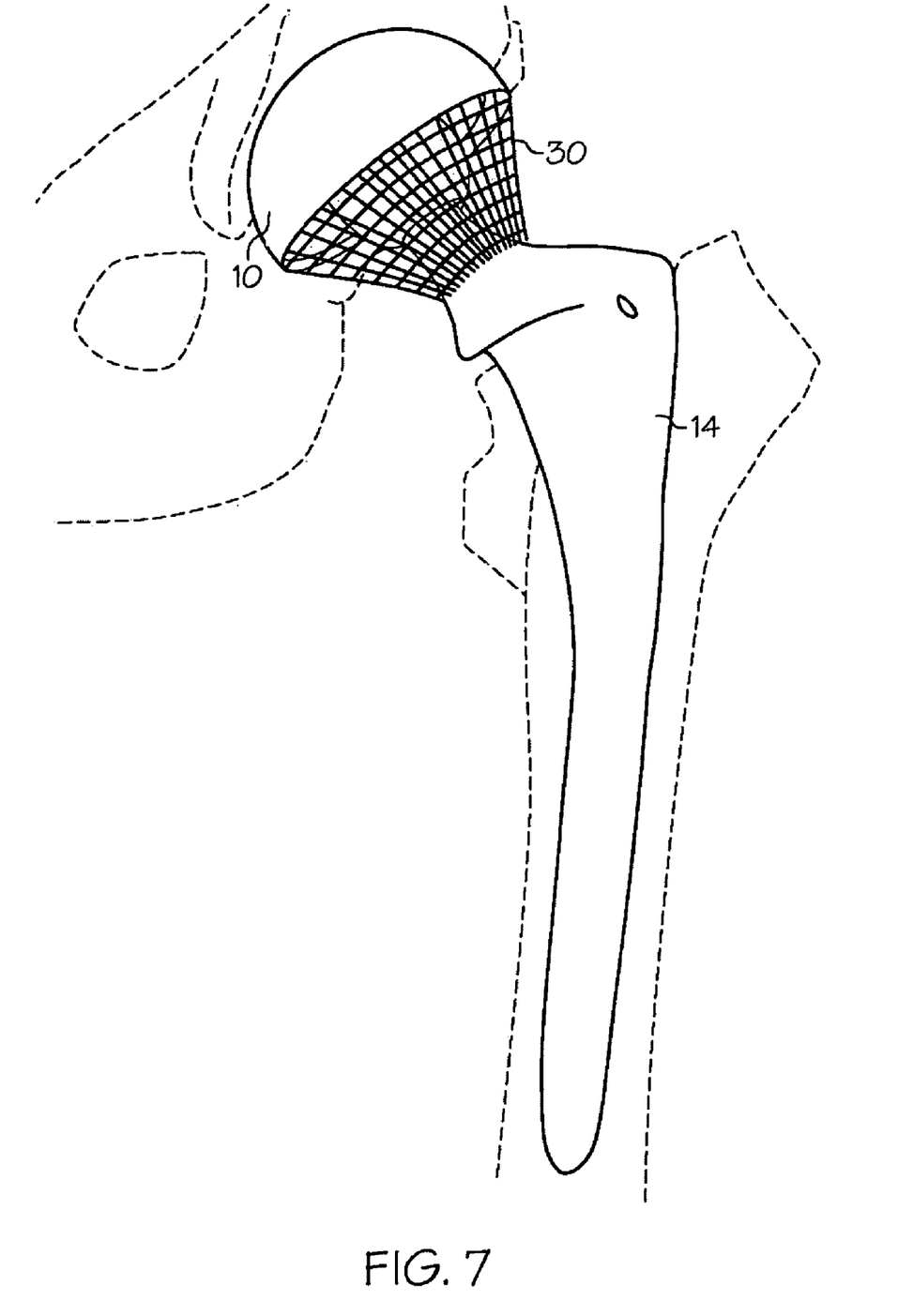
FIG. 7 is a perspective view of a second exemplary embodiment of the present invention mounted to the acetabular prosthetic cup and the femoral component.

In another alternate exemplary embodiment, as shown in FIG. 7, biologic and/or biologically reabsorbable mesh or webbing 30 could be used to hold the mid-neck region of the femoral component 14 to the acetabular shell 10 or to the acetabulum. Examples of biologic and biologically reabsorbable mesh or webbing materials for use in the present embodiment include, without limitation, extra cellular matrices (ECMs). Examples of ECMs include, without limitation, porcine small intestine submucosa (SIS), xenogeneic small intestine submucosa (xSIS), urinary bladder submucosa (UBS), laminated intestinal submucosa, glutaraldehyde-treated bovine pericardium (GLBP), VICRYL (polyglactin 910), collagen, and natural gut. (See e.g. Tissue Engineering, February, 2002, pp. 63-71; Tissue Engineering, June, 2001, pp. 321-34; J. Biomed. Material Resources, November, 2000, pp. 365-73; J Biomed Material Resources, July 2001, pp. 101-8; Arthroscopy, February, 2001, pp. 151-9; Endothelium, 2001, pp. 11-24; Biomaterials, October, 2001, pp. 2653-9; J. Surg. Res., August, 1997, pp. 179-86). By way of example, porcine small intestinal submucosa (SIS) may act as scaffolding for ingrowth of connecter tissue between the acetabular shell 10 and femoral component 14. The mesh 30 may be attached between the femur and/or femoral component 14 (including the neck and ball 22) and at least one of the constraining ring 24, acetabular shell 10, acetabular insert 20, or surrounding bone. Attachment of the mesh 30 to any of the above components could be accomplished by way of suture, suture anchor, screw, rivet, or any other effective fastening mechanism or procedure. An exemplary mounting procedure might include a circumferential channel within the neck of the femoral component 14 being lined by a suture incorporated into the mesh 30, with the suture drawn taught around the neck of the femoral component 14 mounting the mesh 30 thereto. Opposite the femoral component, the mesh 30 may be mounted to the acetabular insert 20 of the acetabular shell 10 with suture anchors. The mesh 30 may be used separately or in combination with the constraining ring 24 discussed above. Again, it will be apparent to those of ordinary skill in the art there are many other biologic and/or biologically reabsorbable materials that can comprise the mesh 30, all of which currently developed and hereafter developed fall within the scope of the invention.

Figure 8:
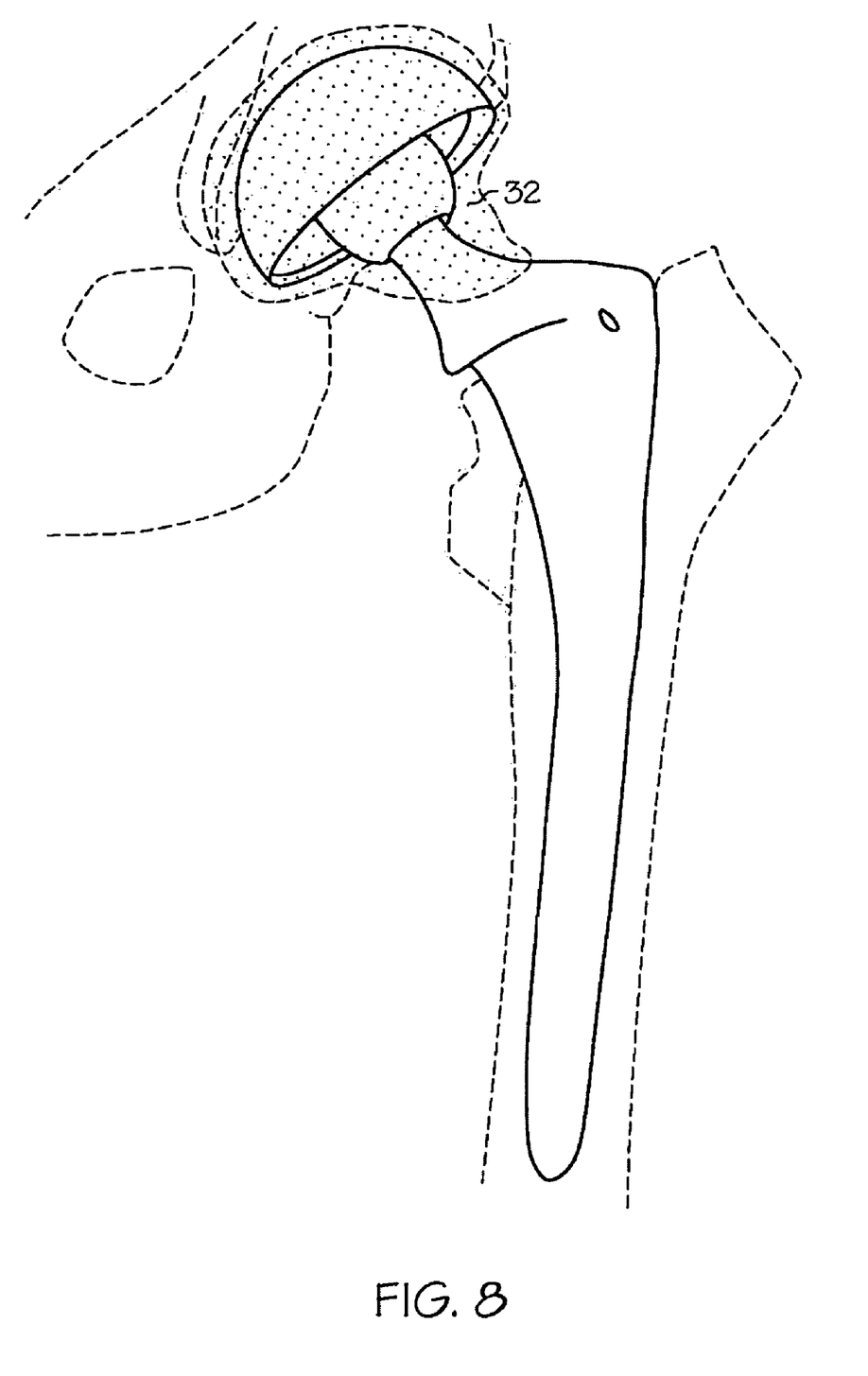
FIG. 8 is a sectional view of a third exemplary embodiment of the present invention positioned in proximity to the acetabular prosthetic cup and the femoral component.

Another exemplary embodiment, as shown in FIG. 8, includes a biologically reabsorbable paste/glue 32 that rapidly converts into tissue (such as scar tissue). The paste/glue 32 is directed in proximity to the neck of the prosthesis and acetabulum and allows patients to decrease the time that they would need to abide by their post-operative hip precautions (such as no tying shoes, donning socks or toenail care). Typically, these precautions prevent the patient from doing any activities that require greater hip flexion than 90°. Examples of materials comprising the biologically reabsorbable paste 32 of the present invention include, for example, without limitation, porcine small intestinal submucosa (SIS) and VICRYL (polyglactin 910). The use of SIS, for example, in a paste form positioned in proximity to the neck region of the prosthesis nearing the end of the arthroplasty could stimulate more rapid tissue formation and substantially decrease the time period before patients could return to normal activities of daily living. It is also within the scope of the invention that agents such as antibiotics and/or clotting agents discussed above could also be added to the paste 32 to decrease the risk of infection in a similar fashion as physicians presently impregnate cement with antibiotics. The paste 32 enables efficient direct delivery of prophylactic antibiotics to the hip joint.

Figure 9:
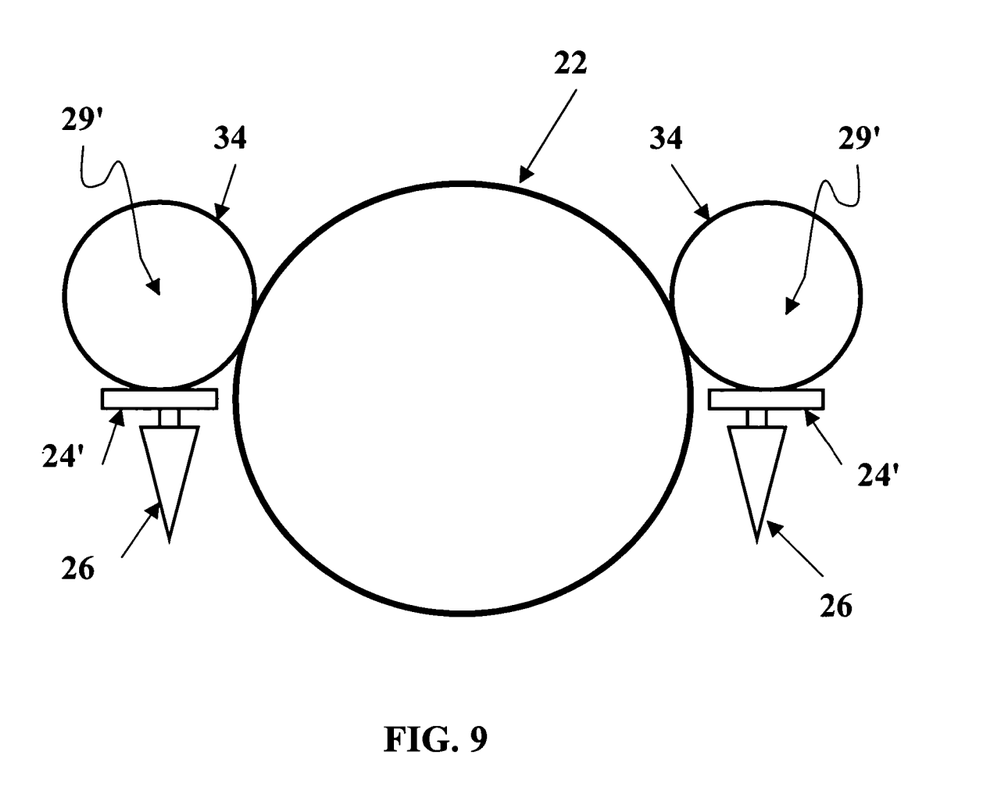
FIG. 9 is a cross sectional view of an alternate exemplary embodiment of the present invention positioned in proximity to the acetabular prosthetic cup and the femoral component.

Referencing FIG. 9, a fourth exemplary embodiment of the present invention includes a constraining ring 24' having a bladder 34 manipulatable to arrive at the cut out regions and the elevations 29' for inhibiting dislocation of the ball 22 from the acetabular insert 20. The constraining is attached to at least one of the acetabular shell, acetabular bone, or to the acetabular insert, through various forms of attachment discussed above, including rivets 26. The bladder 34 may be configured to receive a reabsorbable fluid material injected therein that rapidly transitions to a solid state, thereby expanding at certain locations to provide one or more elevations 29', and providing little or no expansion to accommodate one or more cut out regions. The transition time between liquid and solid state may further enable a physician to custom mold the bladder 34 to inhibit luxation and minimize impingement. Likewise, the constraining ring 24' may have a plurality of bladders 34 to create two or more elevations 29'. It is within the scope of the invention that the bladder 34 be porous, biologic or biologically absorbable, or a combination of these. Further, it is within the scope of the invention that the bladder 34 and/or the contents include one or more agents to promote tissue formation, fight infection, and promote clotting.

With each of the above embodiments, it is within the scope of the invention to incorporate growth stimulating factors with the biologic or biologically reabsorbable materials. These could be incorporated into a bioreabsorbable paste or moldable scaffolding to provide a three dimensional framework for the creation of tissue engineered scar mass inhibiting dislocation of the femoral component 14. Examples of such growth stimulating factors include, without limitation, growth factor beta (GFB-β), basic fibroblast growth factor (bFGF), fibroblast growth factor (FGF), epidermal growth factor (EFG), transforming growth factor-β1 (TGF-β1), vascular endothelial growth factor (VEGF), connective tissue growth factor (CTGF), platelet-derived growth factor (PDGF), direct-mediated gene transfer, fibroblast-mediated gene transfer, myoblast-mediated gene transfer, TGF-β gene family, adenovirus-mediated gene transfer, recombinant adenovirus-induced tendon adhesion formation, BMP-12, bone morphogenetic protein-2 gene transfer, growth and differentiation factor-5 (GDF-5) and, insulin like growth factor (IFG). (See e.g. Koski et al., "Tissue-Engineered Ligament— Cells, Matrix, and Growth Factors", July 2000 Tissue Engineering in Orthopedic Surgery, Volume 31, No. 3), (see e.g., Boyer, "Using Growth Factors to Enhance Tendon and Ligament Repair", Orthopaedic Research Society Symposia, AAOS Annual Meeting New Orleans February 2003). Several of these growth factors have been proposed as possible mitogens in fibroblast growth.

It is also within the scope of the invention to incorporate connective tissue stem cells and progenitors with the biologic or biologically reabsorbable materials disclosed in the above embodiments. These connective tissue stem cells and progenitors may be incorporated into a bioreabsorbable paste 32 or moldable scaffolding to provide a three dimensional framework for the creation of engineered tissue for, in an exemplary application, inhibiting dislocation of the femoral component 14. Examples of such connective tissue stem cells and progenitors include, without limitation, fibroblastic colony-forming cells, fibroplast colony-forming units (CFU-F), bone marrow stromal cells, mesenchymal stem cells (MSC), and vascular pericytes. (See e.g. Meschler et al. "Connective Tissue Progenitors: Practical Concepts for Clinical Applications", 2002 Clinical Orthopaedics and Related Research, No. 395, pp. 66-80).

It is also within the scope of the invention to incorporate hematopoietic stem cells and progenitors with the biologic or biologically reabsorbable materials disclosed in the above embodiments. These hematopoietic stem cells and progenitors may be incorporated into a reabsorbable paste or moldable scaffolding to provide any cell making up circulating blood and the immune system for, in an exemplary application, inhibiting infection after surgery.

It is also within the scope and spirit of the present invention to provide a constraining ring 24 as described herein comprising a biologically non-absorbable material, such as, without limitation, polymers, metals, ceramics, resins, and composites.

Constraining rings 24 comprising biologically non-absorbable materials may be mounted in a like manner as a reabsorbable constraining ring, but with non-absorbable fasteners, such as, without limitation, clips, snaps, screws, sutures, glues or rivets. These non-absorbable constraining rings 24 may have a planar distal surface that includes one or more depressions positioned axially thereabout for increasing the angular range of motion of the femoral component 14. In such a configuration, the axial range of motion of the femoral component 14 may be maintained in all 360° without substantially changing the amount of surface area in contact between the neck of the femoral component 14 and the distal surface of the constraining ring 24. Such constraining rings 24 may also include elevations 29 as discussed above.

It is additionally within the scope and spirit of the present invention to provide a constraining ring 24 comprising a biologic, biologically reabsorbable, and/or biologically non-absorbable material that allows a physician to manipulate the cut out regions 28 and the elevations 29 approximate the cut out regions 28 before and during surgery to better accommodate the patient's unique biomechanics as a result of the hip surgery. An exemplary embodiment may enable manipulation of the elevations 29 and cut out regions 28 by providing a keyway with segmented elevations 29 and cut out regions 28 moving therein. Likewise, an exemplary elevation 29 might be manipulatable by mounting a biologic, biologically reabsorbable, and/or biologically non-absorbable material in the form of a contoured augment onto the distal surface of the constraining ring 24. It is likewise within the scope and spirit of the present invention to allow a physician to manipulate the dimensions and locations of biologic and/or biologically reabsorbable fasteners (such as a clip, snap, screw, suture, keyway, or rivet) utilized to secure the constraining ring 24, elevations 29, or mesh 30 to any of the above structural components.

It is further within the scope and spirit of the present invention to provide a constraining ring 24 having a non-circular aperture. Likewise it is within the scope and spirit of the present invention to provide a constraining ring 24 having a non-circular cross section.

Following from the above description and invention summaries, it should be apparent to those of ordinary skill in the art that, while the apparatuses and methods herein described constitute exemplary embodiments of the present invention, it is to be understood that the inventions contained herein are not limited to these precise embodiments and that changes may be made to them without departing from the scope of the inventions as defined by the claims. Additionally, it is to be understood that the invention is defined by the claims and it is not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A constraining device for, at least temporarily, maintaining engagement of a prosthetic femoral stem component with a prosthetic acetabular component of a prosthetic hip assembly, the constraining device comprising a reabsorbable material taken from the group consisting essentially of a biologic material, a biological material, and a combination of biologic and biological-materials, wherein the material is in the form of a mesh adapted to be attached between the prosthetic acetabular component and the prosthetic femoral stem component, and wherein the constraining device includes a suture.

2. A constraining device for, at least temporarily, maintaining engagement of a prosthetic femoral stem component with a prosthetic acetabular component of a prosthetic hip assembly, the constraining device comprising a reabsorbable material taken from the group consisting essentially of a biologic material, a biological material, and a combination of biologic and biological materials, wherein the material is in the form of a webbing adapted to be attached between the prosthetic acetabular component and the prosthetic femoral stem component, and wherein the constraining device includes a suture.

3. A constraining device for, at least temporarily, maintaining engagement of a prosthetic femoral stem component with a prosthetic acetabular component of a prosthetic hip assembly, the constraining device comprising a reabsorbable material taken from the group consisting essentially of a biologic material, a biological material, and a combination of biologic and biological materials, wherein the material is in the form of a band attached between the prosthetic acetabular component and the prosthetic femoral stem component, and wherein the constraining device includes a suture.

4. An implantable constraining device for, at least temporarily, maintaining integrity of a hip joint, the constraining device comprising a reabsorbable material and a suture, wherein the material is at least one of in the form of a mesh adapted to be attached between a hip bone and a femur, in the form of a webbing adapted to be attached between the hip bone and the femur, and in the form of a band attached between the hip bone and the femur, wherein the reabsorbable material is loaded with at least one of an antibacterial agent, a clotting agent, an agent to promote the formation of scar tissue, an agent to limit the formation of bone tissue, connective tissue-stem cells, connective tissue stem cell progenitors, hematopoietic stem cells, hematopoietic stem cells progenitors and a growth stimulating factor.

5. The prosthetic constraining device of claim 4, wherein the connective tissue stem cells and connective tissue stem progenitors are taken from the group consisting of: fibroblastic colony-forming cells, fibroplast colony-forming units (CFU-F), bone marrow stromal cells, mesenchymal stem cells (MSC), and vascular pericytes.

6. The prosthetic constraining device of claim 4, wherein the material is loaded with a growth stimulating factor.

7. The prosthetic constraining device of claim 6, wherein the growth stimulating factor is taken from the group consisting of: growth factor beta (GFB-β), basic fibroblast growth factor (bFGF), fibroblast growth factor (FGF), epidermal growth factor (EFG), transforming growth factor-β1(TGF-β1), vascular endothelial growth factor (VEGF), connective tissue growth factor (CTGF), platelet-derived growth factor (PDGF), direct-mediated gene transfer, fibroblast-mediated gene transfer, myoblast-mediated gene transfer,TGF-βgene family, adenovirus-mediated gene transfer, recombinant adenovirus-induced tendon adhesion formation, BMP-12, bone morphogenetic protein-2 gene transfer, growth and differentiation factor-5 (GDF-5), and insulin like growth factor (IFG).

* * * * *